(12) United States Patent
Bannister et al.

(10) Patent No.: US 11,457,831 B2
(45) Date of Patent: Oct. 4, 2022

(54) MEDICAL IMAGING SYSTEM AND METHOD

(71) Applicant: Micrima Limited, Bristol (GB)

(72) Inventors: Peter Romilly Bannister, Bristol (GB); Dennis Smith, Bristol (GB); Kevin Leslie Thomas, Bristol (GB)

(73) Assignee: Micrima Limited, Bristol (GB)

( * ) Notice: Subject to any disclaimer, the term of this patent is extended or adjusted under 35 U.S.C. 154(b) by 497 days.

(21) Appl. No.: 16/321,306

(22) PCT Filed: Jul. 28, 2017

(86) PCT No.: PCT/GB2017/052218
§ 371 (c)(1),
(2) Date: Jan. 28, 2019

(87) PCT Pub. No.: WO2018/020270
PCT Pub. Date: Feb. 1, 2018

(65) Prior Publication Data
US 2019/0167145 A1    Jun. 6, 2019

(30) Foreign Application Priority Data
Jul. 29, 2016 (GB) .................................... 1613119

(51) Int. Cl.
*A61B 5/0507* (2021.01)
*A61B 17/34* (2006.01)
(Continued)

(52) U.S. Cl.
CPC .......... *A61B 5/0507* (2013.01); *A61B 5/7485* (2013.01); *A61B 10/0041* (2013.01);
(Continued)

(58) Field of Classification Search
CPC ..... A61B 5/0507; A61B 5/7485; A61B 90/11; A61B 90/37; A61B 90/50; A61B 34/20;
(Continued)

(56) References Cited

U.S. PATENT DOCUMENTS

| 5,211,165 A | 5/1993 | Dumoulin et al. |
| 5,308,321 A | 5/1994 | Castro |

(Continued)

FOREIGN PATENT DOCUMENTS

| JP | 2007061359 A | 3/2007 |
| JP | 2009125280 A | 6/2009 |

(Continued)

OTHER PUBLICATIONS

U.S. Appl. No. 16/638,543 (Year: 2020).*
(Continued)

*Primary Examiner* — Sean D Mattson
(74) *Attorney, Agent, or Firm* — Honigman LLP (57) ABSTRACT

A medical imaging system including a microwave antenna array having a transmitting antenna and a plurality of receiving antennae, wherein the transmitting antenna is configured to transmit microwave signals so as to illuminate a body part of a patient and the receiving antennae are configured to receive the microwave signals following scattering within the body part; a processor configured to process the scattered microwave signals and generate an output indicative of the internal structure of the body part to identify a region of interest within the body part; and a biopsy device comprising a biopsy needle movable relative to the microwave antenna array; wherein the receiving antennae are further configured to receive microwave signals scattered or emitted by the biopsy needle and the processor is further configured to monitor a position of the (Continued)

biopsy needle and to guide the biopsy needle to the identified region of interest within the body part.

13 Claims, 7 Drawing Sheets

(51) Int. Cl.
| | |
|---|---|
| A61B 10/02 | (2006.01) |
| A61B 90/11 | (2016.01) |
| A61B 34/20 | (2016.01) |
| A61B 90/00 | (2016.01) |
| A61B 34/30 | (2016.01) |
| A61B 90/50 | (2016.01) |
| A61B 5/00 | (2006.01) |
| A61B 10/00 | (2006.01) |

(52) U.S. Cl.
 CPC ...... *A61B 10/0233* (2013.01); *A61B 17/3403* (2013.01); *A61B 34/20* (2016.02); *A61B 34/30* (2016.02); *A61B 90/11* (2016.02); *A61B 90/37* (2016.02); *A61B 90/50* (2016.02); *A61B 2017/3411* (2013.01); *A61B 2034/2051* (2016.02); *A61B 2034/2065* (2016.02); *A61B 2090/397* (2016.02); *A61B 2562/0228* (2013.01)

(58) Field of Classification Search
 CPC ... A61B 34/30; A61B 10/0041; A61B 10/233; A61B 10/02; A61B 17/3403; A61B 2562/0228; A61B 2090/397; A61B 2017/3411; A61B 2034/2051; A61B 2034/2065
 See application file for complete search history.

(56) References Cited

U.S. PATENT DOCUMENTS

| | | | | |
|---|---|---|---|---|
| 5,678,549 | A * | 10/1997 | Heywang-Koebrunner | A61B 90/10 600/417 |
| 6,009,878 | A * | 1/2000 | Weijand | A61B 5/06 128/899 |
| 6,546,279 | B1 * | 4/2003 | Bova | A61B 8/0833 600/410 |
| 2004/0143150 | A1 * | 7/2004 | Barzell | A61B 17/3403 600/7 |
| 2007/0249901 | A1 * | 10/2007 | Ohline | A61B 5/068 600/117 |
| 2009/0015832 | A1 * | 1/2009 | Popovic | A61B 5/05 356/342 |
| 2009/0281419 | A1 * | 11/2009 | Troesken | A61B 90/98 600/424 |
| 2010/0030107 | A1 * | 2/2010 | Hancock | A61M 5/158 600/567 |
| 2011/0237937 | A1 | 9/2011 | Kalpin et al. | |
| 2011/0261180 | A1 * | 10/2011 | Simon | G01S 5/0252 348/77 |
| 2013/0303895 | A1 * | 11/2013 | Littrup | A61B 8/403 600/424 |
| 2015/0073259 | A1 | 3/2015 | Zhou et al. | |
| 2016/0022309 | A1 * | 1/2016 | Allaway | A61B 8/0841 600/464 |
| 2017/0140559 | A1 * | 5/2017 | Kim | G06T 11/005 |

FOREIGN PATENT DOCUMENTS

| | | |
|---|---|---|
| JP | 2012511941 A | 5/2012 |
| JP | 2013515567 A | 5/2013 |
| JP | 2014504918 A | 2/2014 |
| JP | 2015527109 A | 9/2015 |
| JP | 2016517296 A | 6/2016 |
| WO | WO-2006080399 A1 | 8/2006 |
| WO | WO-2006106927 A1 | 10/2006 |
| WO | WO-2010143691 A1 | 12/2010 |

OTHER PUBLICATIONS

U.S. Appl. No. 16/638,593 (Year: 2020).*
International Search Report for Application PCT/GB2017/052218 dated Nov. 3, 2017.
Combined Search and Examination Report for Application GB1613119.5 dated Jan. 30, 2017.
Japanese Office Action for Application No. 2019-504788 dated Jun. 23, 2020 (along with English translation).
European Office Action, Application No. 17 748 899.6 dated May 10, 2021.

* cited by examiner

MEDICAL IMAGING SYSTEM AND METHOD

BACKGROUND

The invention relates to a medical imaging system and method and particularly, although not exclusively, to an apparatus and method which incorporates biopsy guidance.

Various medical imaging techniques are known for examining the human body. Such imaging techniques may be used to interrogate tissues and organs in order to identify abnormalities, such as tumors or lesions. For example, X-ray (mammography), microwave imaging, ultrasound, MRI are all common imaging modalities. Once a region of interest has been identified, a biopsy may be taken of the area in order to diagnose whether the tumor is cancerous, for example. Such techniques are commonly used to examine breast tissue, but may also be used in other areas of the body, such as the liver, pancreas, prostate, thyroid, lungs, ovaries and lymph nodes.

The invention seeks to provide a system which improves the accuracy of biopsies taken after the identification of a region of interest.

SUMMARY

In accordance with an aspect of the invention, there is provided a medical imaging system comprising: a microwave antenna array comprising a transmitting antenna and a plurality of receiving antennae, wherein the transmitting antenna is configured to transmit microwave signals so as to illuminate a body part of a patient (human or other animal) and the receiving antennae are configured to receive the microwave signals following scattering within the body part; a processor configured to process the scattered microwave signals and generate an output indicative of the internal structure of the body part to identify a region of interest within the body part; and a biopsy device comprising a biopsy needle movable relative to the microwave antenna array; wherein the receiving antennae are further configured to receive microwave signals scattered or emitted by the biopsy needle and the processor is further configured to monitor a position of the biopsy needle as it is guided to the identified region of interest within the body part.

The processor may be configured to simultaneously generate an output indicative of the internal structure of the body part and monitor the position of the biopsy needle relative to the body part.

The system may comprise a display for displaying a graphical representation of the internal structure body part. The display may also be for displaying a graphical representation of the biopsy needle. The graphical representation of the biopsy needle may be based on the microwave signals scattered or emitted by the biopsy needle. The display may be configured to simultaneously display a graphical representation of both the body part and the biopsy needle relative to one another. The display may be configured to display a representation of the internal structure body part and/or a graphical representation of the biopsy needle in real-time.

The processor may be further configured to guide the biopsy needle to the identified region of interest within the body part.

The microwave antenna array may be formed on a substrate, wherein the substrate comprises one or more openings configured to receive the biopsy needle to provide access to the body part.

The openings may be conical.

The openings may be provided with sealing gaskets.

The openings may comprise one or more slots.

The substrate may comprise a plurality of said openings and wherein the processor is configured to select one of the plurality of openings for introducing the biopsy needle.

The biopsy device may be mounted on an articulated arm configured to maneuver the biopsy device relative to the antenna array.

The articulated arm may be a robotic arm.

The biopsy needle may be configured to emit microwave signals which are received by the receiving antennae.

The biopsy needle may comprise a coaxial feed line which transmits the microwave signals.

The biopsy needle may comprise a microwave marker at its tip.

The processor may perform a first data acquisition and analysis operation when identifying the region of interest and may perform a second data acquisition and analysis operation when guiding the biopsy needle, the second data acquisition and analysis operation may be faster than the first data acquisition and analysis operation.

In accordance with another aspect of the invention, there is provided a medical imaging method comprising: illuminating a body part of a patient with microwave signals emitted by a transmitting antenna of an microwave antenna array; receiving the microwave signals following scattering within the body part at a plurality of receiving antennae of the microwave antenna array; processing the scattered microwave signals to generate an output indicative of the internal structure of the body part; identifying a region of interest within the body part from the output; and guiding a biopsy needle to the identified region of interest within the body part by monitoring microwave signals scattered or emitted by the biopsy needle using the receiving antennae.

BRIEF DESCRIPTION OF THE DRAWINGS

For a better understanding of the invention, and to show more clearly how it may be carried into effect, reference will now be made, by way of example, to the accompanying drawings, in which.

DETAILED DESCRIPTION

Figure 1:
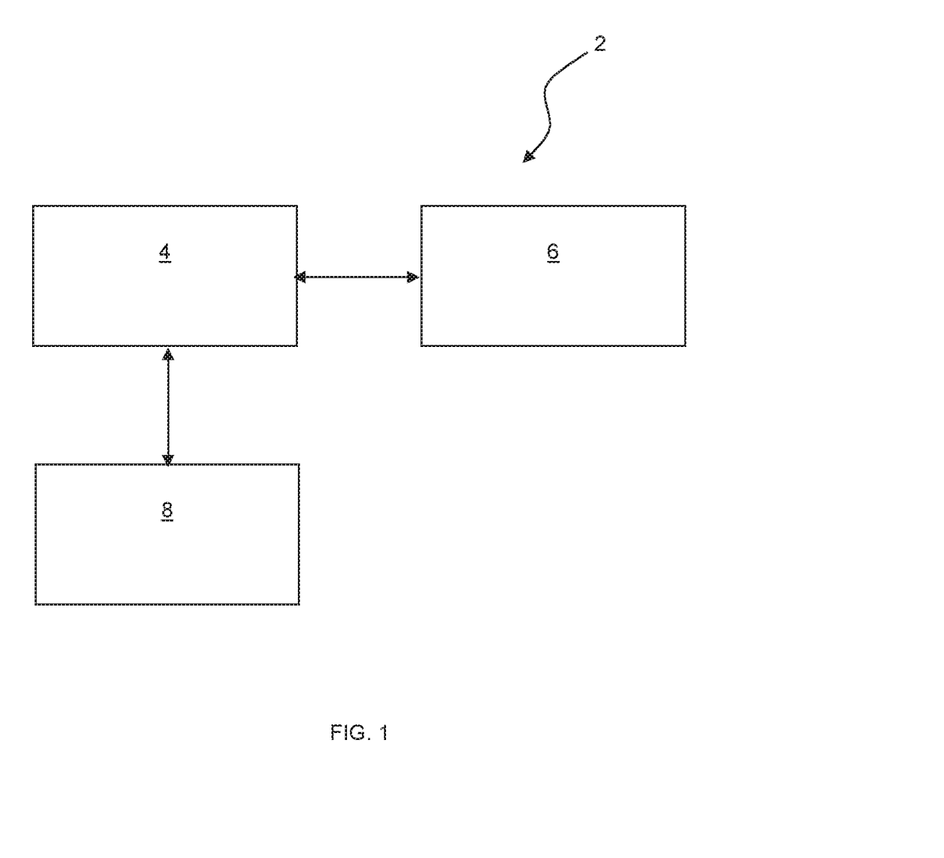
FIG. 1 is a system diagram of a medical imaging system according to an embodiment of the invention.

FIG. 1 shows a medical imaging system 2 according to an embodiment of the invention. The medical imaging system generally comprises a processor 4, a microwave antenna array 6 in communication with the processor 4, and a biopsy device 8 in communication with the processor 4.

Figure 2:
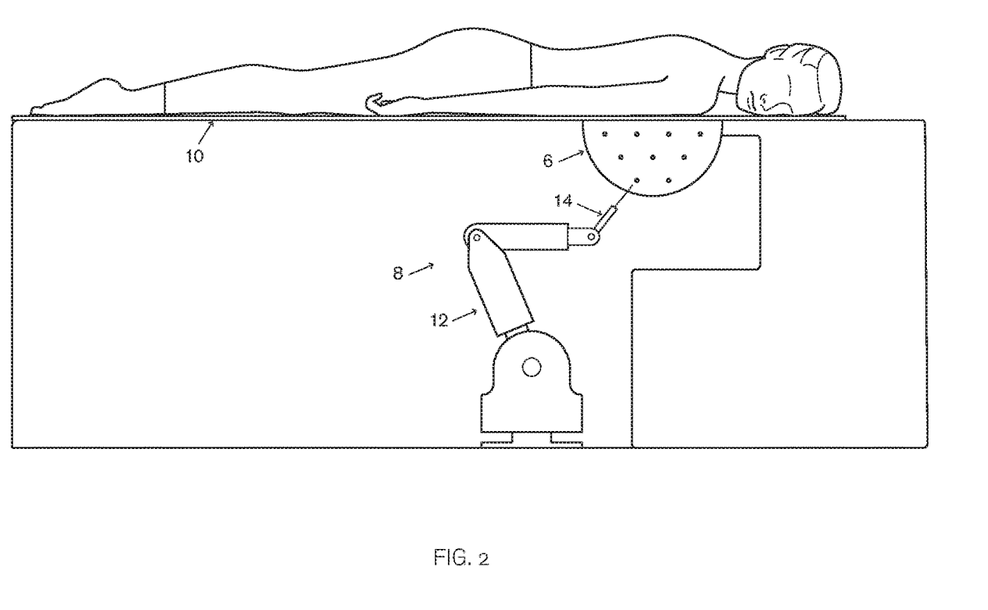
FIG. 2 is a schematic side view of an example implementation of the medical imaging system.

As shown in FIG. 2, the microwave antenna array 6 may form part of a table 10 on which a patient lies in a prone position. The biopsy device 8 is connected to the table 10 or otherwise located in a fixed or known position relative to the table 10. The biopsy device 8 comprises an articulated arm 12 which carries a biopsy gun 14. The articulated arm 12 allows the biopsy gun 14 to be maneuvered relative to the antenna array 6.

Figure 3:
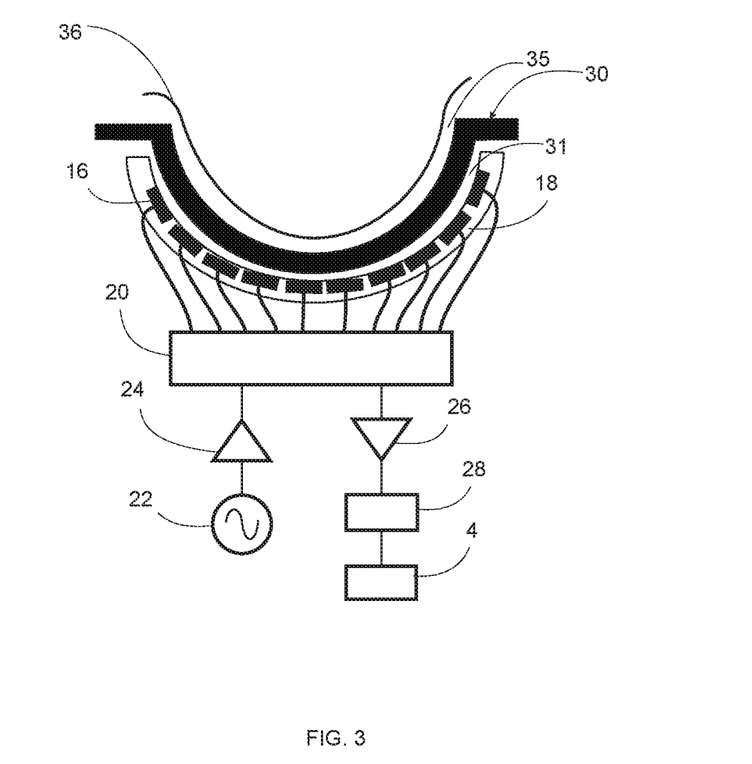
FIG. 3 is a schematic view of imaging portion of the medical imaging system.

As shown in FIG. 3, the antenna array 6 comprises a plurality N of antennae 16 which are arranged over the surface of, or within, a shell substrate 18. The shell 18 has a curved profile as shown. In particular, the shell 18 is part or hemi-spherical and is configured to approximate the shape of a breast. The antennae 16 are arranged over the shell 18 such that they all point to a common focal point.

The antennae 16 are each electrically connected to a switching matrix 20. The switching matrix 20 is in turn connected to both a transmit path and a receive path. The transmit path comprises a signal generator 22 coupled to an amplifier 24. The receive path comprises an amplifier 26 coupled to a detector 28 and the processor 4.

The switching matrix 20 selectively couples each of the antennae 16 to either the transmit path or the receive path.

The antenna array 6 is operated in a multi-static fashion. Specifically, the switching matrix 20 is controlled so as to connect one of the antennae 16 to the transmit path and the remaining antennae 16 to the receive path. The signal generator 22 generates a stepped frequency continuous wave (CW) signal which is amplified by the amplifier 24 and then transmitted by the antenna 16 connected to the transmit path. The stepped frequency continuous wave signal is a sequential series of pulses of continuous wave energy, where each pulse has its frequency stepped up across a range of frequencies, typically within the 3-8 GHz range. The other antennae 16 receive the transmitted signal and the received signal is detected and then recorded by the processor 4.

Figure 4:
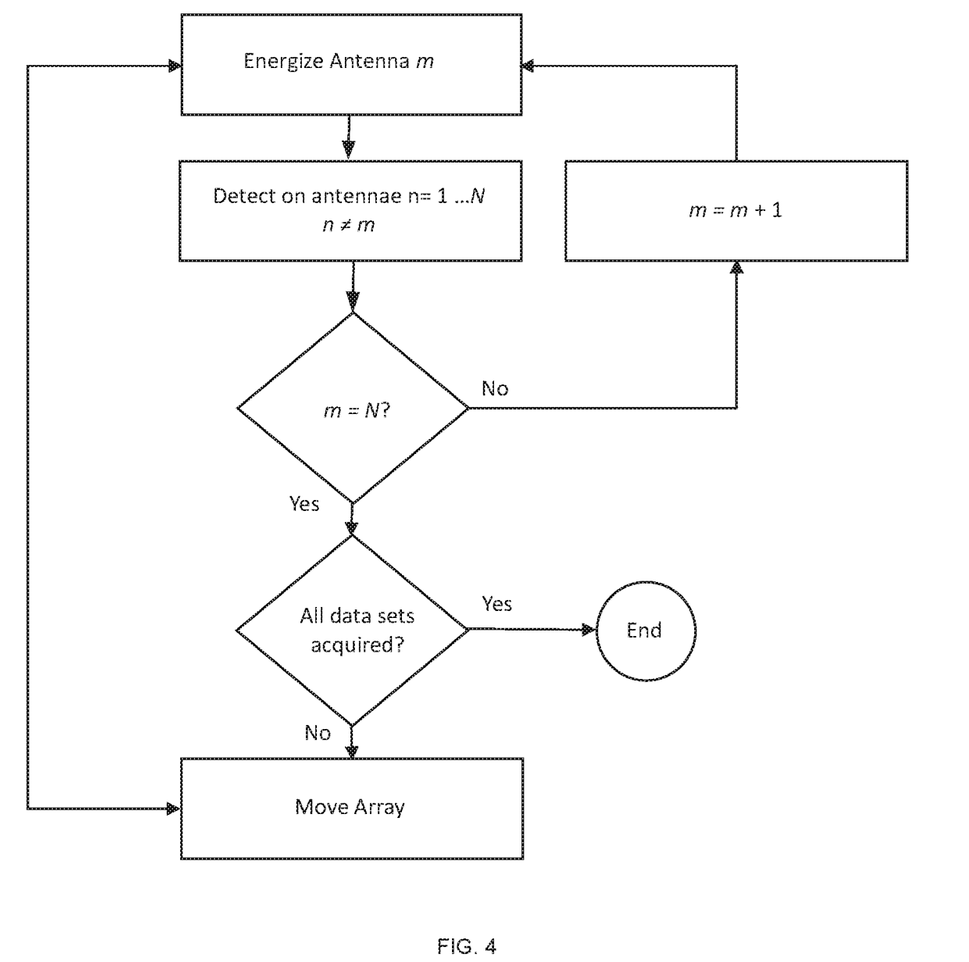
FIG. 4 is a flowchart depicting a sampling method.

FIG. 4 shows a flowchart of a data acquisition method. As shown, the switching matrix 20 connects an antenna m of the N antennae to the transmit path. All other antennae 16 (n=1 ... N, n≠m) are connected to the receive path and detect the transmitted signal (possibly in a time-sharing arrangement). If m≠N, the switching matrix 20 steps to the next antenna 16 (m=m+1) to be connected to the transmit path. This is repeated until all antennae 16 have been connected to the transmit path. The acquisition process may be repeated with the antenna array 6 translated (i.e. rotated about its rotational axis). This may allow fixed errors to be cancelled from the detected signals.

Referring again to FIG. 3, the shell 18 receives a cup 30. The cup 30 has a complementary shape to the shell 18 such that if fits snugly within the shell 18.

The outside of the cup 30 and the inside of the shell 18 may have threaded portions to enable a threaded engagement between the cup 30 and the shell 18. The threaded engagement between the cup 30 and the shell 18 may be used to translate the antenna array 6 relative to the breast 36, as described previously.

A layer of coupling fluid (dielectric constant controlled fluid) may be inserted in the gap 31 between the shell 18 and the cup 30 so as to improve the coupling between the antennae 16 and the cup 30 in order to minimize signal loss and thus improve transmission of the microwave signal.

Figure 5:
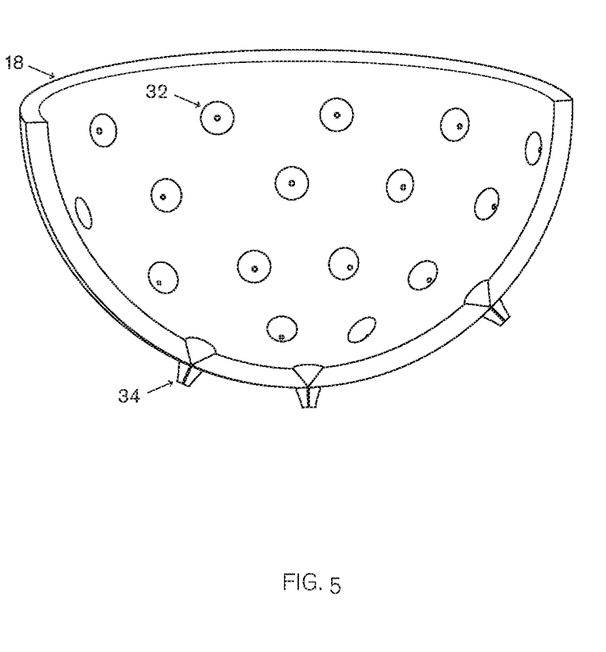
FIG. 5 is perspective cross-sectional view of an antenna shell of the medical imaging system.

As shown in FIG. 5, the shell 18 comprises a plurality of apertures 32 which are distributed across the surface of the shell 18. Each aperture 32 extends through the thickness of the shell 18 and tapers such that the aperture 32 is wider at the inner surface of the shell 18 than at the outer surface. The apertures 32 are therefore frustoconical. Each aperture 32 is provided with a sealing nozzle or gasket 34. The gaskets 34 are provided in order to prevent the coupling fluid from leaking through the apertures 32. The cup 30 also comprises a set of corresponding apertures in order to provide access from the exterior of the shell 18 through to the interior of the cup 30.

In use, a patient lies on the table 10 in a prone position such that their breast 36 sits in the cup 30. A layer of coupling fluid may also be provided in the gap 35 between the cup 30 and the breast 36 in order to improve coupling between the antennae 16 and the breast 36.

Although not shown, one or more inserts may be placed inside the cup 30 so as to enable a better fit between the internal surface of the cup 30 and the breast 36. For example, a plurality of such inserts may be provided, each having different shapes and sizes, to enable the system to be better adapted to breasts of different shapes and sizes. The inserts may be made from the same material as the cup (e.g. ceramic).

The antenna 16 connected to the transmit path illuminates the breast 36 with the microwave signal. The signal is scattered by the breast tissue and the scattered signal is received at each of the non-transmitting antennae 16 where it is detected and recorded. This process is repeated for each antenna 16, as described previously with reference to the data acquisition method shown in FIG. 4.

The processor 4 may record the relative difference between the measured phase and amplitude of the transmitted signal as compared to the phase and amplitude of the scattered signal, recorded as a complex number (having real and imaginary parts).

The signal detected at each antenna 16 will generally comprise three components: a component arising from mutual coupling between the transmitting and receiving antennas 16; a component arising from radiation which reflects off the skin of the breast 36; and a component arising from radiation which reflects off structures within the breast (such as tumors). Tumors can generate identifiable reflections as they exhibit much higher dielectric properties than adipose tissues due to their significant water content. The mutual and skin reflection components may be removed or at least mitigated from the data set in order to improve the detectability of reflections resulting from the presence of tumors within the breast.

The acquired data set may be used by the processor 4 to construct an image of the internal structure of the breast 36. Data reconstruction may be performed using Phased Array (frequency domain), Delay and Sum (DAS—time domain) techniques or any other suitable technique. From this, the processor 4 is able to identify (possibly, with additional user input or confirmation) a region of interest (if present) in which a possible tumor or other pathology may exist.

Once the processor 4 has identified the region of interest, the biopsy device may be used to provide a biopsy of the region of interest. In particular, the processor 4 may guide the articulated arm 12 so as to locate the biopsy gun 14 in the desired position and orientation for accessing the region of interest. The articulated arm 12 may be a robotic arm such that it can manipulate the biopsy gun 14 to the required position and orientation based on coordinates provided by the processor 4. Alternatively, the articulated arm 12 may be actuated by a user but provide feedback via appropriate sensors to the user or processor 4 of its current position so that it can be brought into the proper position and orientation. As a further alternative, the articulated arm 12 may be dispensed with and the biopsy gun 14 itself provide feedback via sensors on its current position and orientation to the processor 4 or user.

As described previously, the shell 18 comprises a plurality of apertures 32 which provide access to the breast 36 for a biopsy needle of the biopsy gun 14. The system may use any form of biopsy needle. As an example, the biopsy needle may comprise an inner stylet which is movably disposed within an outer cutting cannula. The biopsy gun 14 may comprise a spring-loaded mechanism which deploys the stylet and cannula in succession either automatically or under user control. The stylet is deployed first and comprises a notch which receives a sample. The cutting cannula is subsequently deployed so as to cut the sample and enclose it within the notch so that the sample can be withdrawn from the patient.

The processor 4 may determine the most appropriate aperture 32 for taking the biopsy. In particular, the processor 4 may determine the closest aperture 32 to the region of interest. As described previously, the apertures 32 are frustoconical such that the biopsy needle can be introduced through the aperture 32 at a range of angles.

With the biopsy gun 14 guided to the appropriate position and orientation for accessing the region of interest, the biopsy needle can be fired into the breast 36. The antenna array 6 can be used to confirm that the biopsy needle is coincident with the region of interest by again illuminating the breast 36 with microwave signals and detecting scattered signals from the biopsy needle. Specifically, the processor 4 may confirm that the biopsy gun 14 is appropriately positioned prior to firing by updating the image. Once this has been confirmed, the articulated arm 12 may be fixed in position. The image of the breast 36 (or only the relevant portion) may be updated as the biopsy needle passes into the breast 36 towards and into the region of interest.

During the biopsy guidance stage, the processor 4 may adjust the signal processing performed such that it is optimized for speed and mapping a known object in space.

After the user has obtained a sample of the region of interest along the trajectory of biopsy needle, the user may then manipulate the biopsy needle to collect additional samples of the region of interest under microwave image guidance, without having to create additional puncture wounds in the skin of tissue.

Biopsy needles are typically made of steel which generally provides a strong microwave scattering signal and can therefore be reliably located. However, the biopsy needle may bend as it passes through tissue, and/or the scattering signal may be modified by surrounding tissue. To allow for either of these more complex cases, the biopsy needle may be modified so that it is more easily identifiable. In particular, the biopsy needle may be provided with a marker which is more easily discriminated by microwave radar in order to determine needle tip location and overall orientation more accurately.

Microwave markers will typically have one or more of the following characteristics:
  Enhanced overall microwave scattering amplitude over surrounding tissue
  Microwave scattering that is a strong function of frequency—the continuous wave radar is well suited to measure scattering as a function of frequency
  Scattering anisotropy—the hemispherical antenna array 6 is able to characterize scattering over a wide solid angle.

The marker should have a distinctive radar signature that can be characterized rapidly for guidance purposes. For example, the marker may include:
  Radio frequency identification tags
  Microwave metamaterials
  Ferromagnetically or ferrimagnetically resonant materials within the UWB band, such as ferrites.

Alternatively, the biopsy needle itself may radiate the microwave signal, rather than scattering signals generated by the antennae 16. For example, the biopsy needle may have an integrated coaxial feed line which supplies the signal to the tip of the needle.

Alternatively, the biopsy needle may comprise an integrated microwave source.

The antennae 16 of the antenna array 6 therefore all (or a subset of the antennae 16) act to receive the signal emitted by the needle. Using the needle as the signal source avoids having to sequentially connect each of the antennae 16 to the transmit path and thus allows the scan time to be drastically reduced, potentially allowing real time operation.

Although the shell 18 has been described as having a plurality of frustoconical apertures 32 for providing access to the breast, other arrangements may be used. In particular, the shell 18 may have a plurality of circumferential slots. The angular spacing of the slots corresponds to the available angular rotation of the antenna array 6. Each slot, under rotation, gives access to a volume of tissue which typically overlaps to some degree with adjacent slots in order to offer some options in needle placement.

Figure 6:
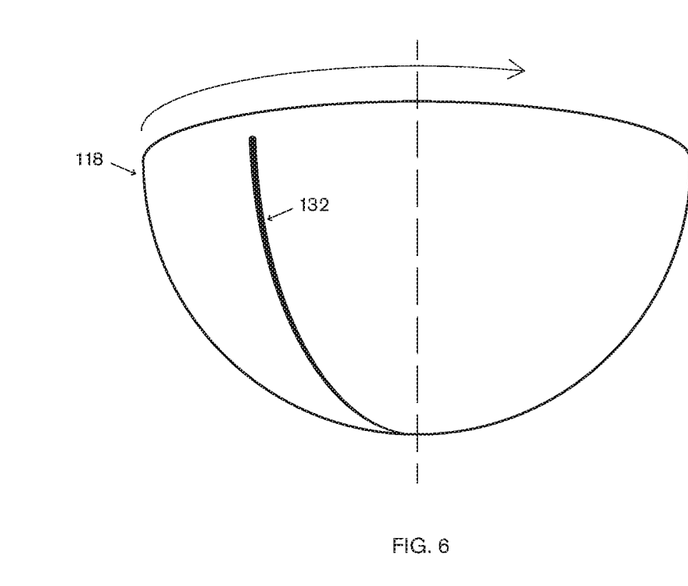
FIG. 6 is a perspective view of an alternative antenna shell used in the medical imaging system.

In particular, FIG. 6 shows an alternative embodiment of a shell 118 which may be used where the antenna array 6 is able to rotate through 180°. The shell 118 comprises a single slot 132 which passes through the axis of rotation from each side of the shell 118 (or two diametrically opposed slots with a discontinuity at the axis of rotation). The shell 118 is rotatable through 180° such that the slot 132 is able to allow the biopsy needle to access the entire breast 36.

Figure 7:
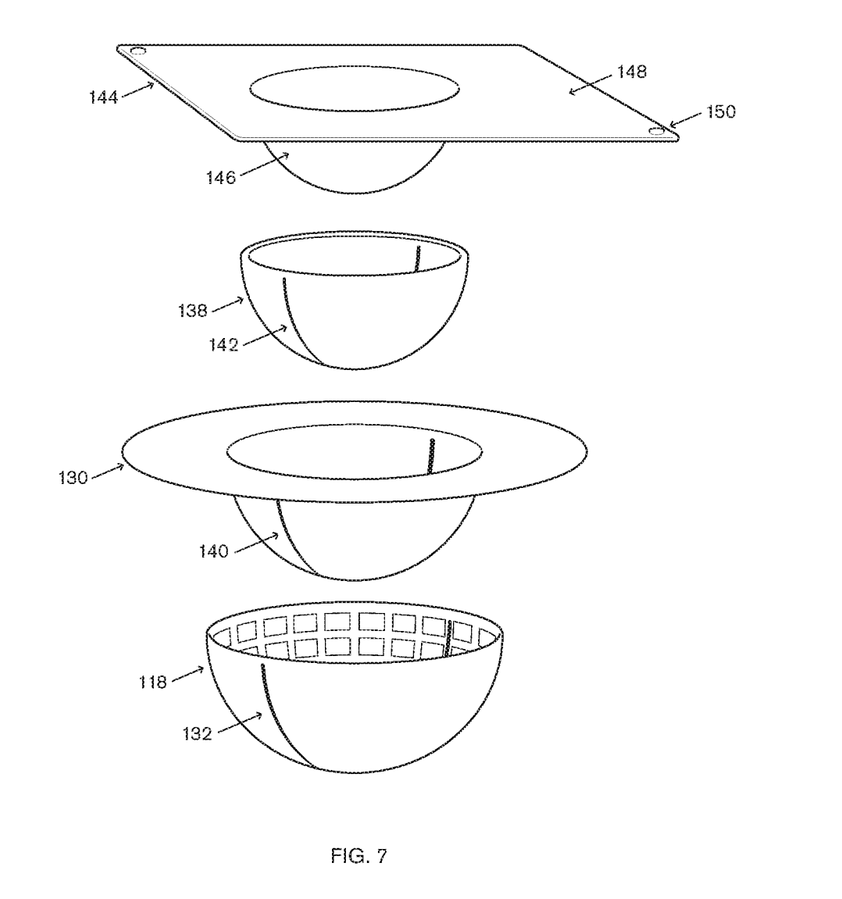
FIG. 7 is an exploded view of an assembly comprising the antenna shell of FIG. 6.

As shown in FIG. 7, the shell 118 is used with a cup 130 and, if required, an insert 138. The cup 130 has a complementary shape to the shell 118 such that if fits snugly within the shell 118 and, in turn, the insert 138 has a complementary shape to the cup 130 such that if fits snugly within the cup 130.

The cup 130 is provided with a slot 140 which corresponds to the slot 132 of the shell 118. Similarly, the insert 138 is provided with a slot 142 which corresponds to the slot 132 of the shell 118. The cup 130 and, if used, the insert 138 are disposed within the shell 118 such that the slots 132, 140, 142 of the shell 118, cup 130 and insert 138 are all aligned with one another. The slots 132, 140, 142 therefore provide access to the breast 36 from the exterior of the shell 118. The cup 130 and insert 138 are connected to the shell 118 so as to prevent relative rotation and thus to maintain the alignment of the slots 132, 140, 142. In particular, the cup and insert may be provided with locating tabs which prevent rotation relative to the shell 118.

As described with respect to the previous embodiment, a layer of coupling fluid may be inserted in the gap between the shell 118 and the cup 130 and also in the gap between the cup 130 and the insert 138. The slots 132, 140, 142 may be fitted with a gasket to prevent the escape of coupling fluid.

To allow the shell 118 to rotate relative to the breast 36, a disposable tray 144 is used. The tray 144 is made from a biocompatible polymer, such as PEEK, HIPS, PET. The tray comprises a central section 146 which is curved to conform to the underlying cup 130 or insert 138. In particular, the central section 146 may be part or hemi-spherical. Disposable trays may be provided in different sizes that correspond to the internal dimensions of each available insert (and cup) respectively so that a low-compliance fit to the underlying surface is achieved. A planar rim 148 extends from the central section 146. The material thickness over the central section 146 may be less than that of the planar rim 148. The planar rim 148 may therefore provide structural rigidity to the disposable tray 144, while the thin central section 146 ensures that the dielectric properties of the matching interface between the cup/inserts and patient is not disturbed.

The disposable tray 144 is held stationary against the breast 36 while the shell 118, cup 130 and insert 138 are rotated to properly align the slots 132, 140, 142 with the desired location over the breast 36 from which to perform the biopsy. The disposable tray 144 may be provided with location tabs 150 or the like which engage with complementary features on a stationary housing (not shown) of the antenna array 6. The disposable tray 144 is therefore fixed in position and prevented from rotating with the shell 118 and the intermediate component(s). The disposable tray 144 provides little resistance to the rotation of the shell 118 and so the patient does not feel the shell 118 being moved into position.

It will be appreciated that the disposable tray 144 lies over the aligned slots 132, 140, 142 and so obstructs the needle of the biopsy gun 14. However, the material of the disposable tray 144 is suitably thin than it can be punctured by the needle. The needle punctures the tray 144 and breast tissue at a sufficiently high speed and force to minimize the breast tissue shrinking away from the surface of the tray 144. This therefore ensures that the needle takes a sample from the determined region of interest. Further, at least over the central section 146, the material of the disposable tray 144 may have low-shear characteristics such that when it is punctured by a biopsy needle, the fracturing characteristic of the polymer can be controlled.

A drainage arrangement may be included to ensure that any coupling fluid that flows out of the slots in the array is channeled away from the main electro-mechanical components of the system.

The system described herein is capable of both providing a clinical breast microwave image showing a suspicious lesion and also locating and guiding a breast biopsy needle to sample tissue based on the position of the lesion.

As the biopsy guidance is performed by the same system which identifies the region of interest, the patient may remain in position throughout the procedure such that the breast retains registration throughout.

The system provides significant benefits over previously known systems and techniques. In particular, the system provides precise positioning of the biopsy needle with respect to the acquired image, so that the clinician has a high degree of confidence that the proposed trajectory of the biopsy needle will intersect the region of interest. This reduces the number of needle insertions/withdrawals and the risk of seeding malignant cells along multiple needle tracks.

Although the system has been described with reference to the imaging of a breast, it will be appreciated that it may be adapted for other areas of the body.

It will be appreciated that the processor 4 need not display, or indeed, generate, an image of the internal structure of the breast in order to identify a region of interest. The region of interest may instead be determined based on the raw data.

In other arrangements, the cup of the antenna array may be dispensed with or integrated into the shell in which the antennae are located.

The system may employ multiple transmit and receive paths, such that data can be recorded from multiple antennas simultaneously, and may even comprise a number of transmit and receive paths corresponding to the number of antennas, such that data can be recorded from all antennas simultaneously. In an alternative topology, the switching matrix could be removed thus allowing each antenna to be connected to a transmitting/receiving device.

Alternatively, more than one antenna may be operated at a time in a frequency multiplexed operation. Multiplexed operation may have significant advantages where high speed tracking of the needle is required.

To avoid unnecessary duplication of effort and repetition of text in the specification, certain features are described in relation to only one or several aspects or embodiments of the invention. However, it is to be understood that, where it is technically possible, features described in relation to any aspect or embodiment of the invention may also be used with any other aspect or embodiment of the invention.

The invention is not limited to the embodiments described herein, and may be modified or adapted without departing from the scope of the present invention.

The invention claimed is:

1. A medical imaging system, comprising:
a microwave antenna array including a plurality of antennae, the plurality of antennae including a transmitting antenna and a plurality of receiving antennae, wherein the transmitting antenna is configured to transmit microwave signals so as to illuminate a body part of a patient and the receiving antennae are configured to receive the microwave signals following scattering of the microwave signals within the body part;
a processor configured to process the scattered microwave signals and generate an output indicative of an internal structure of the body part to identify a region of interest within the body part; and
a biopsy device including a biopsy needle movable relative to the microwave antenna array;
wherein the microwave antenna array is embedded within a substrate, wherein the substrate includes one or more openings configured to receive the biopsy needle to provide access to the body part each of the one or more openings extending through the substrate so as to be disposed Between the plurality of antennae in the microwave antenna array;
wherein the receiving antennae are further configured to receive microwave signals scattered or emitted by the biopsy needle and the processor is further configured to monitor a position of the biopsy needle as it is guided to the identified region of interest within the body part.

2. A medical imaging system as claimed in claim 1, wherein the processor is further configured to guide the biopsy needle to the identified region of interest within the body part.

3. A medical imaging system as claimed in claim 1, wherein the one or more openings are conical.

4. A medical imaging system as claimed in claim 1, wherein the one or more openings are provided with sealing gaskets.

5. A medical imaging system as claimed in claim 1, wherein the one or more openings comprise one or more slots.

6. A medical imaging system as claimed in claim 1, wherein the substrate comprises a plurality of said one or more openings and wherein the processor is configured to select one of the plurality of openings for introducing the biopsy needle.

7. A medical imaging system as claimed in claim 1, wherein the biopsy device is mounted on an articulated arm configured to maneuver the biopsy device relative to the microwave antenna array.

8. A medical imaging system as claimed in claim 7, wherein the articulated arm is a robotic arm.

9. A medical imaging system as claimed in claim 1, wherein the biopsy needle is configured to emit microwave signals which are received by the plurality of receiving antennae.

10. A medical imaging system as claimed in claim 9, wherein the biopsy needle comprises a coaxial feed line which transmits the microwave signals.

11. A medical imaging system as claimed in claim 1, wherein the biopsy needle comprises a microwave marker at a tip of the biopsy needle.

12. A medical imaging system as claimed in claim 1, wherein the processor performs a first data acquisition and analysis operation when identifying the region of interest and performs a second data acquisition and analysis operation when guiding the biopsy needle, the second data acquisition and analysis operation being faster than the first data acquisition and analysis operation.

13. A medical imaging method comprising:
  illuminating a body part of a patient with microwave signals emitted by a transmitting antenna of a microwave antenna array, wherein the microwave antenna array is formed on a substrate and wherein the substrate includes one or more openings configured to receive a biopsy needle to provide access to the body part;
  receiving the microwave signals following scattering of the microwave signals within the body part at a plurality of receiving antennae of the microwave antenna array;
  processing the scattered microwave signals to generate an output indicative of an internal structure of the body part;
  identifying a region of interest within the body part from the output;
  receiving the biopsy needle through one of the one or more openings and between the antennae in the microwave antenna array; and
  guiding the biopsy needle to the identified region of interest within the body part by monitoring microwave signals scattered or emitted by the biopsy needle using the receiving antennae.

* * * * *